(12) United States Patent
Farris et al.

(10) Patent No.: US 10,842,643 B2
(45) Date of Patent: Nov. 24, 2020

(54) UNIDIRECTIONAL DYNAMIC INTERBODY FUSION DEVICE AND METHOD OF USE

(71) Applicant: BioSpine, LLC, Columbia City, IN (US)

(72) Inventors: Jeffrey A. Farris, Berne, IN (US); Daniel Refai, Atlanta, GA (US); Brian G. Emerick, Columbia City, IN (US); Ross R. Nichols, North Webster, IN (US)

(73) Assignee: BioSpine, LLC, Columbia City, IN (US)

( * ) Notice: Subject to any disclaimer, the term of this patent is extended or adjusted under 35 U.S.C. 154(b) by 0 days.

(21) Appl. No.: 16/207,703

(22) Filed: Dec. 3, 2018

(65) Prior Publication Data
US 2019/0099278 A1 Apr. 4, 2019

Related U.S. Application Data

(63) Continuation of application No. 14/753,503, filed on Jun. 29, 2015, now Pat. No. 10,143,565, which is a (Continued)

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/447* (2013.01); *A61F 2/4425* (2013.01); *A61F 2/4465* (2013.01); *A61F 2/4611* (2013.01); *A61F 2002/2835* (2013.01); *A61F 2002/304* (2013.01); *A61F 2002/3052* (2013.01); *A61F 2002/3055* (2013.01); *A61F 2002/30398* (2013.01); *A61F 2002/30401* (2013.01); *A61F 2002/30405* (2013.01); *A61F 2002/30523* (2013.01); *A61F 2002/30556* (2013.01); *A61F 2002/30579* (2013.01); *A61F 2002/30594* (2013.01); *A61F 2002/30601* (2013.01); (Continued)

(58) Field of Classification Search
CPC .................... A61F 2/44–447; A61F 2/4611
See application file for complete search history.

(56) References Cited

U.S. PATENT DOCUMENTS

| 4,951,519 A | 8/1990 | Ohtsuka |
|---|---|---|
| 6,719,796 B2 | 4/2004 | Cohen et al. |

(Continued)

*Primary Examiner* — Nicholas J Plionis
*Assistant Examiner* — Steven J Cotroneo
(74) *Attorney, Agent, or Firm* — Heslin Rothenberg Farley & Mesiti P.C.

(57) ABSTRACT

An interbody fusion device includes a top member, a base member, and an expansion member. The top member includes a first bone-engaging side and a threaded opening. The base member is received by the top member and includes a second bone-engaging side and an open cavity aligned with the threaded opening of the top member. The expansion member is disposed within the open cavity for rotation about an axis. The expansion member includes a threaded portion threadably engaged with the threaded opening. Rotation of the expansion member translates the first bone-engaging side away from the second bone-engaging side along the axis.

17 Claims, 13 Drawing Sheets

Related U.S. Application Data continuation of application No. 13/487,927, filed on Jun. 4, 2012, now Pat. No. 9,066,813.

(60) Provisional application No. 61/493,239, filed on Jun. 3, 2011.

(51) Int. Cl.
*A61F 2/30* (2006.01)
*A61F 2/28* (2006.01)

(52) U.S. Cl.
CPC ............ *A61F 2002/30604* (2013.01); *A61F 2002/30607* (2013.01); *A61F 2002/30616* (2013.01); *A61F 2002/30785* (2013.01); *A61F 2002/30904* (2013.01); *A61F 2310/00017* (2013.01); *A61F 2310/00023* (2013.01)

(56) References Cited

U.S. PATENT DOCUMENTS

| | | |
|---|---|---|
| 7,584,682 B2 | 9/2009 | Hsiao |
| 7,708,779 B2 | 5/2010 | Edie |
| 7,981,157 B2 | 7/2011 | Castleman et al. |
| 8,303,663 B2 | 11/2012 | Jimenez |
| 8,377,140 B2 * | 2/2013 | DeFalco .................. A61F 2/44 254/100 |
| 9,066,813 B2 | 6/2015 | Farris et al. |
| 2005/0234555 A1 * | 10/2005 | Sutton .................. A61F 2/4455 623/17.15 |
| 2005/0261769 A1 * | 11/2005 | Moskowitz ............. A61F 2/441 623/17.11 |
| 2006/0004447 A1 * | 1/2006 | Mastrorio .......... A61B 17/7065 623/17.11 |
| 2006/0058877 A1 * | 3/2006 | Gutlin ....................... A61F 2/44 623/17.11 |
| 2006/0149385 A1 * | 7/2006 | McKay ................. A61F 2/4455 623/17.15 |
| 2007/0049943 A1 * | 3/2007 | Moskowitz ........ A61B 17/0642 606/279 |
| 2007/0191954 A1 * | 8/2007 | Hansell .................... A61F 2/442 623/17.15 |
| 2007/0198089 A1 * | 8/2007 | Moskowitz ............. A61F 2/442 623/17.11 |
| 2007/0233254 A1 * | 10/2007 | Grotz ..................... A61F 2/442 623/17.11 |
| 2007/0255407 A1 * | 11/2007 | Castleman ................ A61F 2/44 623/17.11 |
| 2007/0255415 A1 * | 11/2007 | Edie .......................... A61F 2/44 623/17.16 |
| 2008/0147193 A1 * | 6/2008 | Matthis ................. A61F 2/4425 623/17.16 |
| 2008/0161933 A1 | 7/2008 | Grotz et al. |
| 2008/0243254 A1 * | 10/2008 | Butler ....................... A61F 2/44 623/17.16 |
| 2009/0112325 A1 * | 4/2009 | Refai .................. A61F 2/30734 623/17.16 |
| 2011/0035011 A1 | 2/2011 | Cain |
| 2011/0160861 A1 * | 6/2011 | Jimenez ............. A61B 17/7065 623/17.16 |
| 2012/0209386 A1 | 8/2012 | Triplett et al. |
| 2012/0310350 A1 | 12/2012 | Farris |

\* cited by examiner

UNIDIRECTIONAL DYNAMIC INTERBODY FUSION DEVICE AND METHOD OF USE

CROSS-REFERENCE TO RELATED APPLICATIONS

This application is a continuation of U.S. patent application Ser. No. 14/753,503 filed on Jun. 29, 2015, (U.S. Pat. No. 1,014,365), which was a continuation of U.S. patent application Ser. No. 13/487,927 filed on Jun. 4, 2012, now U.S. Pat. No. 9,066,813, which claims the benefit of U.S. Provisional Application No. 61/493,239, filed on Jun. 3, 2011. The entire disclosures of each of the above applications are incorporated herein by reference.

FIELD

The present invention relates generally to general surgery, orthopaedic and neurosurgical implants used for insertion within a space between hard tissue structures, and more specifically, but not exclusively, concerns devices implanted between bones to replace a resected, fractured or diseased structures and to maintain or reestablish proper spacing between two bones.

BACKGROUND

This section provides background information related to the present disclosure which is not necessarily prior art.

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY

According to one aspect, the present disclosure provides an interbody fusion device. The interbody fusion device may include a top member, a base member, and an expansion member. The top member may include a first bone-engaging side and a threaded opening. The base member may be received by the top member and may include a second bone-engaging side and an open cavity aligned with the threaded opening of the top member. The expansion member may be disposed within the open cavity for rotation about an axis. The expansion member may include a threaded portion threadably engaged with the threaded opening. Rotation of the expansion member may translate the first bone-engaging side away from the second bone-engaging side along the axis.

According to another aspect, an interbody fusion device is provided. The interbody fusion device may include a top member, a base member, and an expansion member. The top member may include a first bone-engaging side and a threaded opening. The base member may be received by the top member and may include a second bone-engaging side and an open cavity in communication with the threaded opening of the top member. The expansion member may be secured within the open cavity for rotation about an axis extending transverse to the first and second bone-engaging sides. The expansion member may include a threaded portion threadably engaged with the threaded opening. Rotation of the expansion member may translate the top member relative to the base member along the axis.

According to yet another aspect of the present disclosure, a surgical method for maintaining a space between two vertebral bodies in a spine with an interbody fusion device having a top member, a base member, and an expansion member is provided. The method may include inserting the interbody fusion device into a space between the two vertebral bodies. The method may also include rotating the expansion member about a first axis extending transverse to a first bone-engaging side of the top member and transverse to a second bone-engaging side of the base member. The method may further include threadably engaging the expansion member with a threaded opening of the top member. The method may also include translating the first bone-engaging side away from the second bone-engaging side along the first axis.

Further, additional features and advantages are realized through the techniques of the present invention. Other embodiments and aspects of the invention are described in detail herein and are considered a part of the claimed invention.

DRAWINGS

The drawings described herein are for illustrative purposes only of selected embodiments and not all possible implementations, and are not intended to limit the scope of the present disclosure.

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

Figure 14:
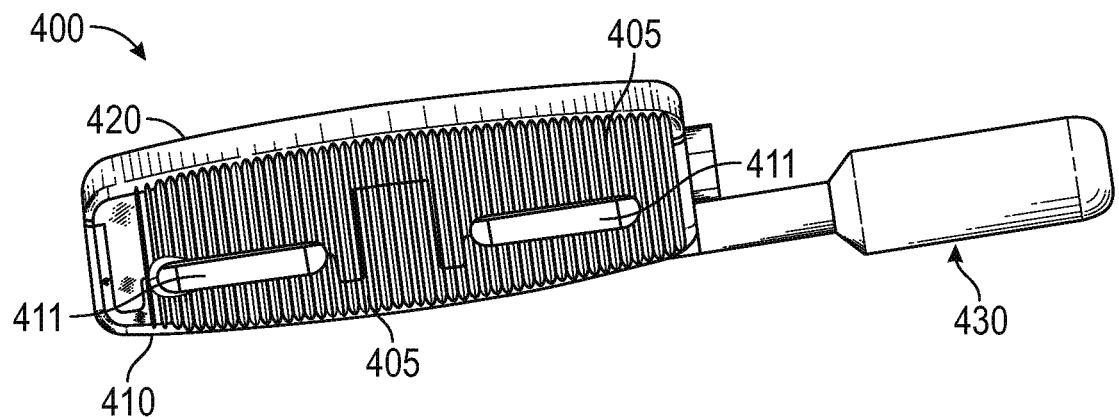
FIG. 14 is a perspective view of another embodiment of a unidirectional, horizontal expandable interbody fusion device, in accordance with an aspect of the present invention.
Figure 17:
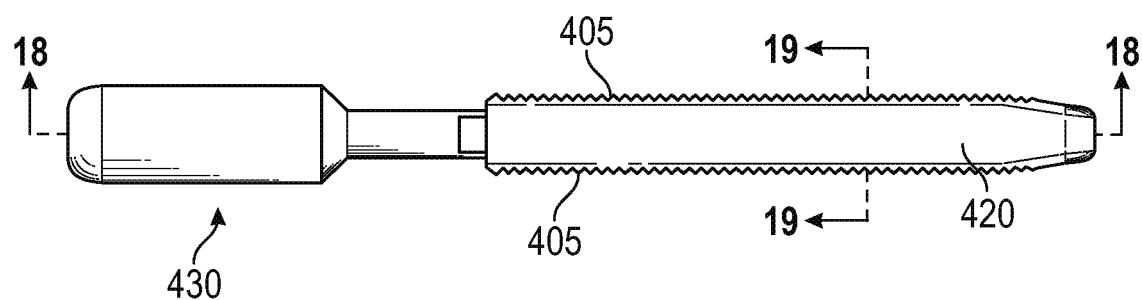
FIG. 17 is a superior view of the expandable interbody fusion device of FIG. 14, in accordance with an aspect of the present invention.
Figure 19:
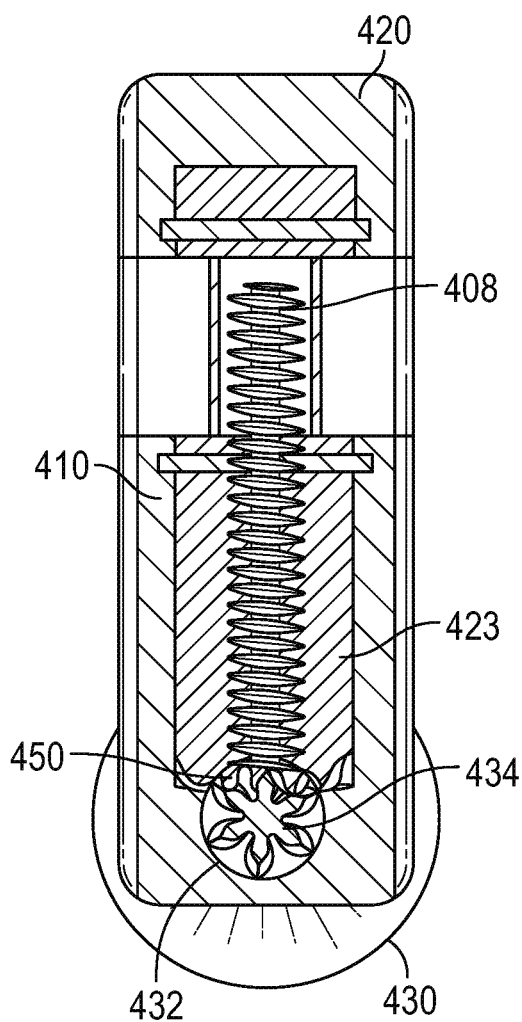
Figure 20:
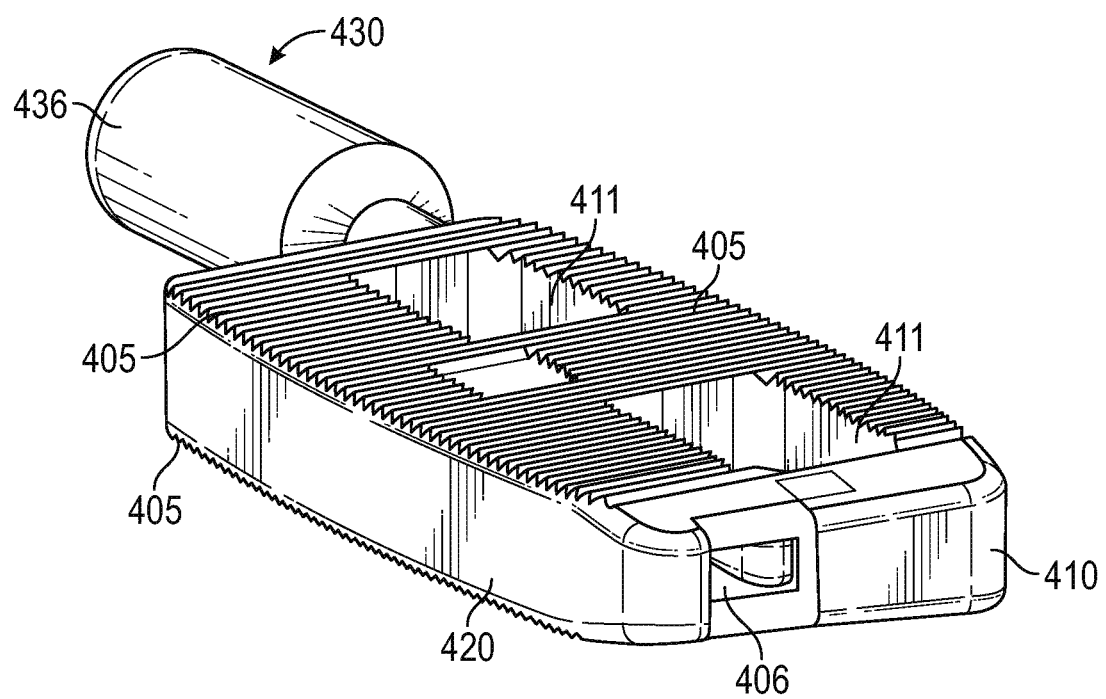

FIG. 19 is an enlarged cross-sectional sagittal plane, elevational view of the expansion/retraction mechanism of the expandable interbody fusion device of FIG. 14 taken along line 19-19 in FIG. 17, in accordance with an aspect of the present invention; and FIG. 20 is a perspective view of the embodiment of the expandable interbody fusion device of FIG. 14, in accordance with an aspect of the present invention.

Corresponding reference numerals indicate corresponding parts throughout the several views of the drawings.

DETAILED DESCRIPTION

Example embodiments will now be described more fully with reference to the accompanying drawings.

Generally stated, disclosed herein is an interbody fusion device or interbody device that typically includes a body/base member, a threaded rod member, a support means, and a retractable member. The retractable member extending either in a horizontal direction or a vertical direction. As used herein, the terms "interbody fusion device," "device," "interbody device," and "implant" may be used interchangeable as they essentially describe the same type of device. Further, a corresponding expansion tool used for expansion and contraction of the interbody device is discussed. Finally, described herein is a surgical method for using the interbody fusion device to maintain a space between two vertebral bodies within a patient suffering from a diseased or damaged disc or spinal column.

Figure 1:
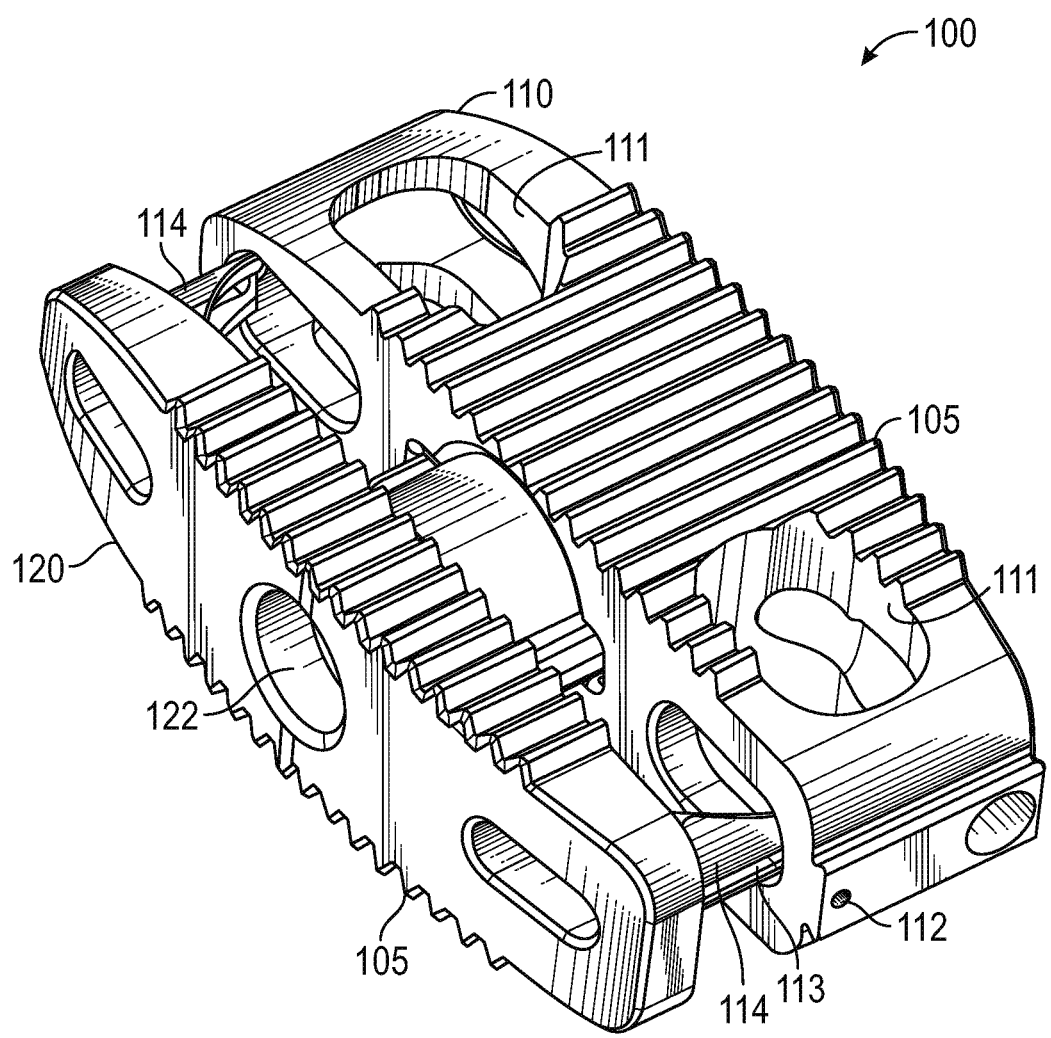
FIG. 1 is a perspective view of one embodiment of a unidirectional, horizontal expandable interbody fusion device, in accordance with an aspect of the present invention.
Figure 7:
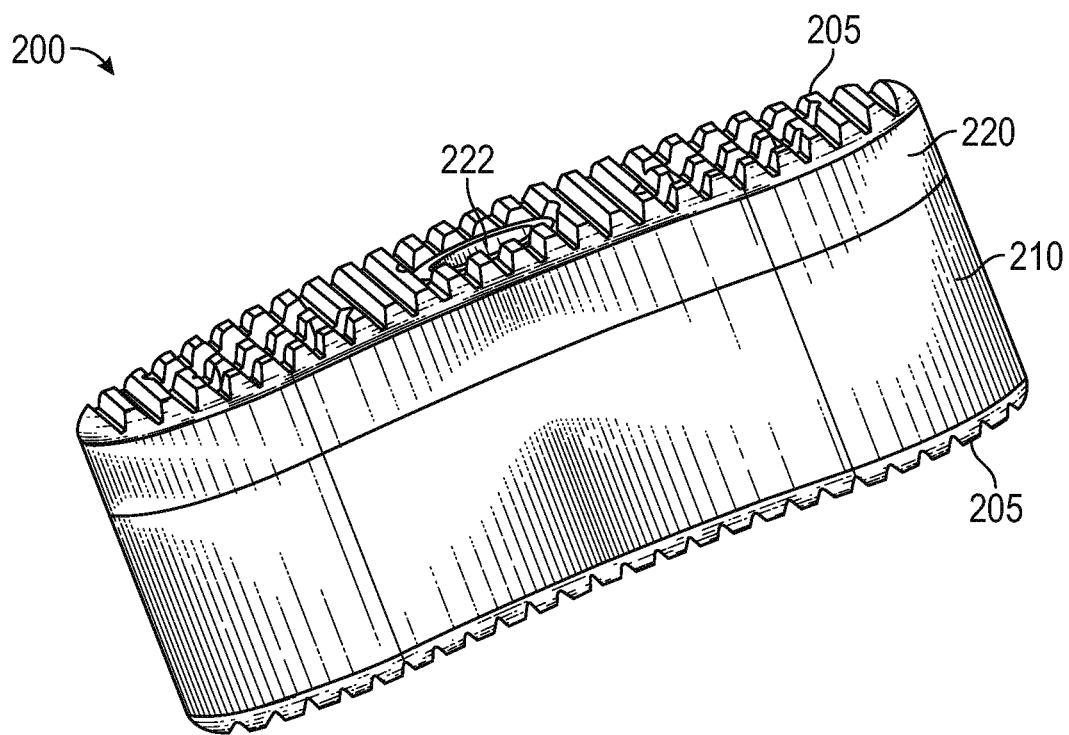
FIG. 7 is a perspective view of one embodiment of a unidirectional, vertical expandable interbody fusion device with the moveable member retracted, in accordance with an aspect of the present invention.

As depicted in FIG. 1, the general arrangement of a unidirectional horizontal expandable interbody fusion device 100, in accordance with an aspect of the present invention, includes a body member 110 and one side member 120. Also shown in FIG. 7 is the general arrangement of a unidirectional vertical expandable interbody fusion device 200, in accordance with an aspect of the present invention that, includes a base member 210 and one superior member 220. Shown in FIG. 14 is a second general arrangement of a unidirectional horizontal expandable interbody fusion device 400, in accordance with an aspect of the present invention that, includes a base member 410 and one side member 420. In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 2:
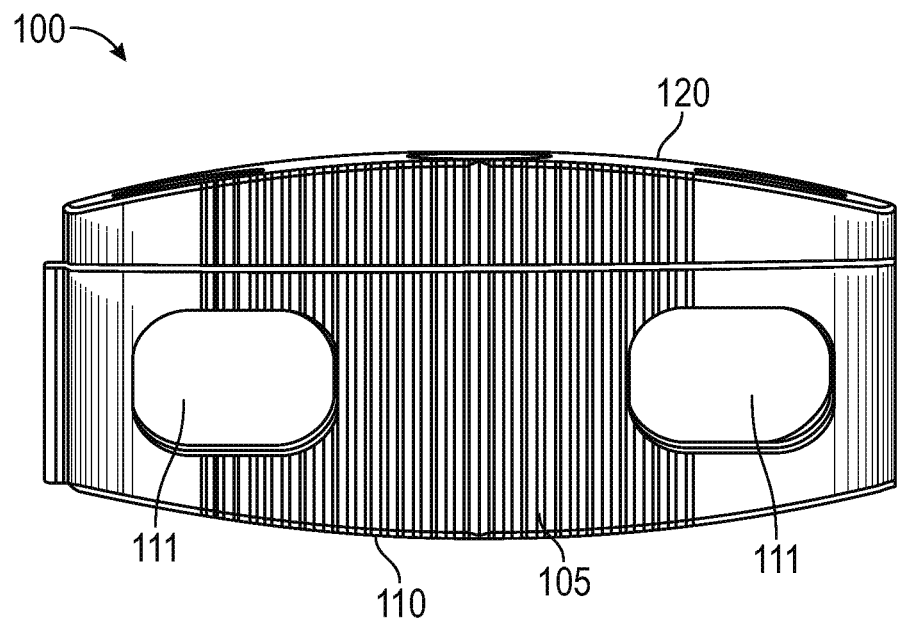
FIG. 2 is a superior view of the expandable interbody fusion device of FIG. 1 with the moveable member retracted, in accordance with an aspect of the present invention.
Figure 3:
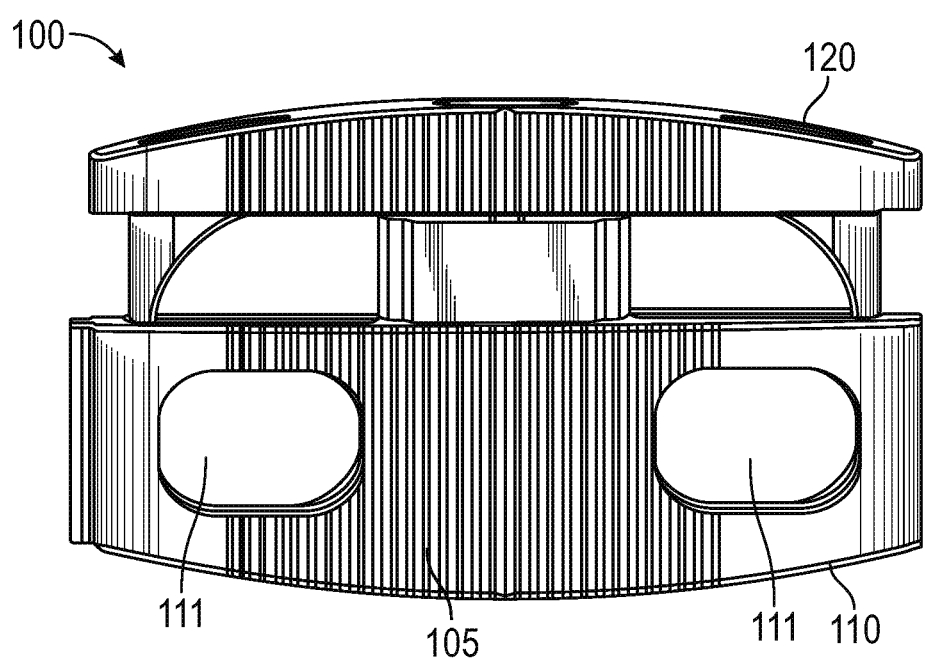
FIG. 3 is a superior view of the expandable interbody fusion device of FIG. 1 with the moveable member extended, in accordance with an aspect of the present invention.

It is shown in FIG. 1, a first example of the unidirectional, horizontal expandable interbody fusion device 100. The device 100 as seen in FIGS. 1 and 2 has a generally rectangular geometry with various configured long sides to facilitate insertion and bone coverage. For example purposes, the long sides are arcuate although it is contemplated that other geometrical shapes may also be used in the construct. The implant 100 may likely include at least one moveable side member 120 and a body member 110. The side member 120 may be detachably coupled to the body member 110.

As seen in FIGS. 1, 2, 3 and 4A-C, body member 110 typically has at least two oval shaped through holes 111 for insertion of bone graft material disposed on the inferior and superior bone contacting surfaces 105. The holes extend through these top and bottom surfaces 105 of the body member 110. These openings 111 typically extend through both bone contacting surfaces 105 and into the inner cavity of the body member 110. The size and configuration of the openings 111 allow the surgeon to place bone graft material inside the implant 100 to achieve a continuous fusion between the inferior and superior vertebral bodies.

Figure 4A:
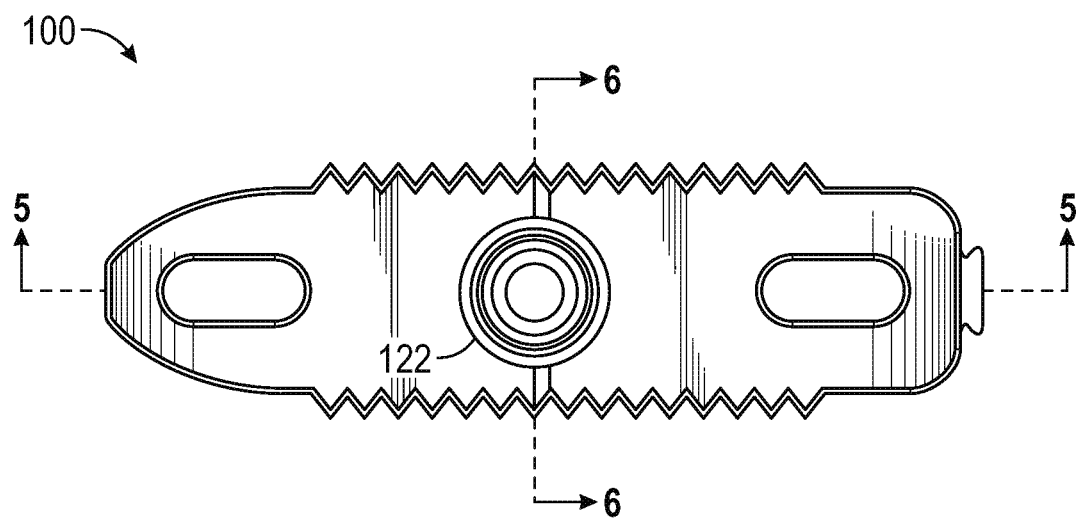
FIG. 4A shows a posterior view of the expandable interbody fusion device of FIG. 1 with the moveable member extended, in accordance with an aspect of the present invention.
Figure 4B:
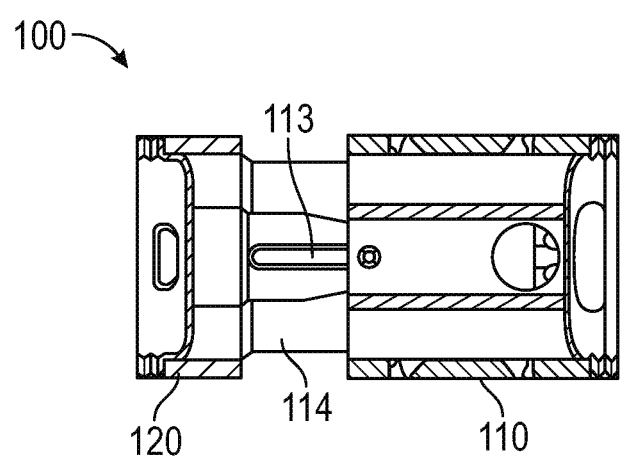
FIG. 4B shows a lateral view of the expandable interbody fusion device of FIG. 1 with the moveable member extended, in accordance with an aspect of the present invention.
Figure 4C:
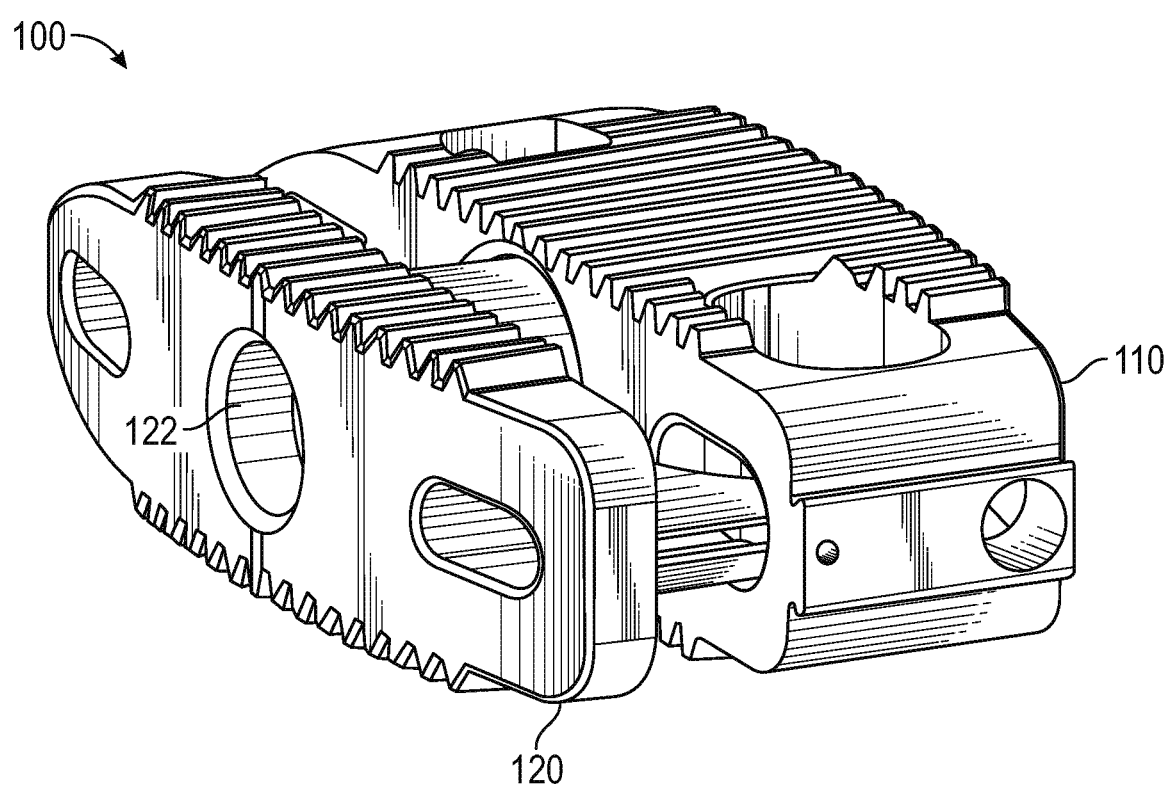
FIG. 4C shows a perspective view of the expandable interbody fusion device of FIG. 1 with the moveable member extended, in accordance with an aspect of the present invention.

As seen in FIG. 4A-C, side member 120 also may have polygonal shaped holes oriented in a horizontal direction. These holes may be encircled by a wall 114 projecting from an inner surface of side member 120 to facilitate the orientation of the side member 120 when it translates from a retracted to an expanded position and vice-a-versa. The wall 114 may also include a horizontal slot 113 though which a stop pin 112 or other mechanism extends to keep the side member from overextending and becoming disengaged with the body member.

Again as shown in FIG. 4A-C, positioned intermediate the oval holes is a means for moving the side member 120. For example purposes, the means for moving the side member may include a threaded circular hole 122 positioned within the side member 120 (also seen in FIG. 1). As shown in sectional views depicted in FIGS. 5 and 6, threaded hole 122 is configured to threadingly engage with threaded rod member 123. Rotation of threaded rod member 123 will cause side member 120 to move either in an inward or outward direction relative to the body member 110. The overall width of the implant 100 can be changed via the rotation of the threaded rod member 123 and the corresponding unidirectional movement of side member 120. It is contemplated that other means for causing the controlled translation of side member 120 to occur may include a ratcheting or locking sliding mechanism.

Also shown in FIGS. 1, 2, 3, and 4A-C are the superior and inferior bone contacting surfaces 105. For example purposes, bone contacting surfaces 105 are shown having teeth-like or tine structures projecting away from the superior and inferior surfaces. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. Further, it is contemplated that angled bone contacting surfaces, caps or plates may be attachable to address various clinical deformities that are encountered clinically. It is also understood that the bone contacting surfaces 105 may be coated with bioactive or bone ingrowth coatings.

As shown in FIGS. 1 and 4A-C, body member 110 has a generally rectangular shape with three through openings passing along the transverse plane. The holes are configured to receive the above discussed walls 114 of the side member 120 as the side member 120 is moved relative to body member 110. The holes are generally positioned in the lateral aspect of body member 110. A centralized through hole 122 that for this embodiment is positioned between the above described horizontal holes is sized to receive the threaded rod member 123 or other means for moving the side member.

Figure 5:
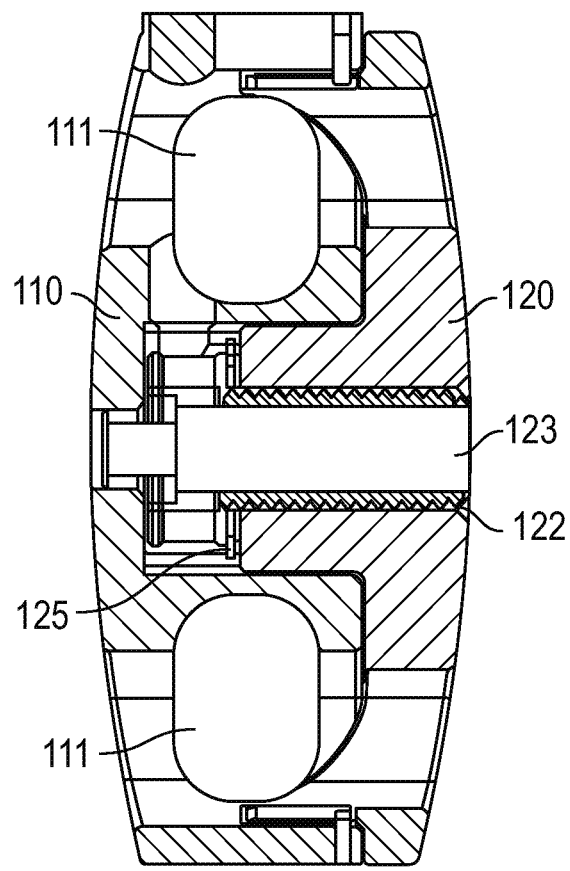
FIG. 5 is a cross-sectional transverse plane, elevational view of one embodiment of the expandable interbody fusion device of FIG. 1 taken along line 5-5 in FIG. 4A, in accordance with an aspect of the present invention.
Figure 6:
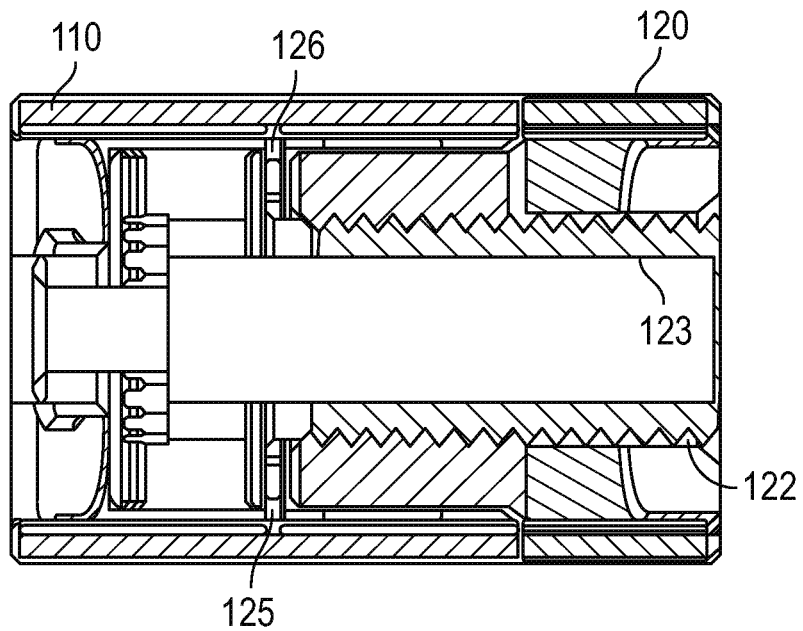
FIG. 6 is an enlarged cross-sectional sagittal plane, elevational view of the expansion/retraction mechanism of the expandable interbody fusion device of FIG. 1 taken along line 6-6 in FIG. 4A, in accordance with an aspect of the present invention.

As shown in the sectional views of FIGS. 5 and 6, the threaded rod member 123 will rotate within the body member 110 while engaging the threaded hole 122 of the side member 120 causing movement thereof. The sectional views of FIGS. 5 and 6 show the threaded rod 123 positioned within the central cavity of body member 110. A support ring 125 acts to couple the threaded rod 123 to maintain the static position of the expansion/retraction mechanism when rotated. Support ring 125 may be a snap ring or other similar type of structure that will nest within a notch 126 or other retainment mode within the inner cavity of the body member 110.

As discussed above and shown in FIG. 1, a stop pin 112 may be used to extend through each of the walls 114 in a medial direction and would be sized to extend into the slot 113 of wall 114 of the side member 120. For example purposes, stop pin 112 is shown as being cylindrical although other shaped stops can be utilized.

Figure 11A:
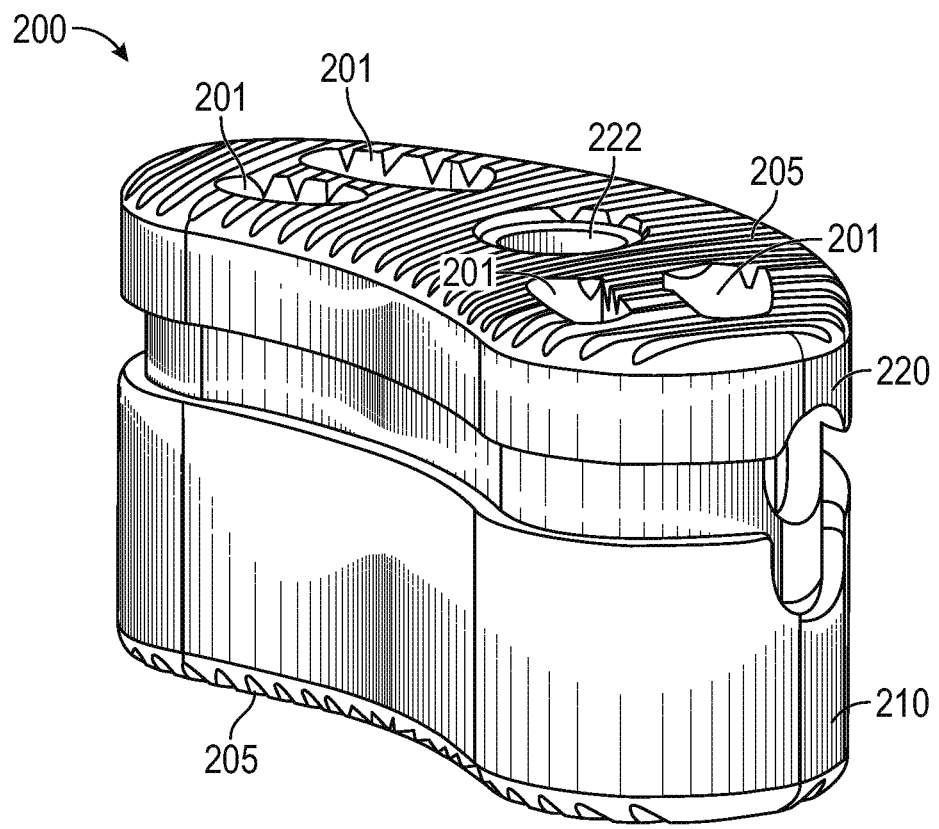
FIG. 11A shows a perspective view of the vertical, expandable interbody fusion device of FIG. 7 with the moveable member extended, in accordance with an aspect of the present invention.
Figure 11B:
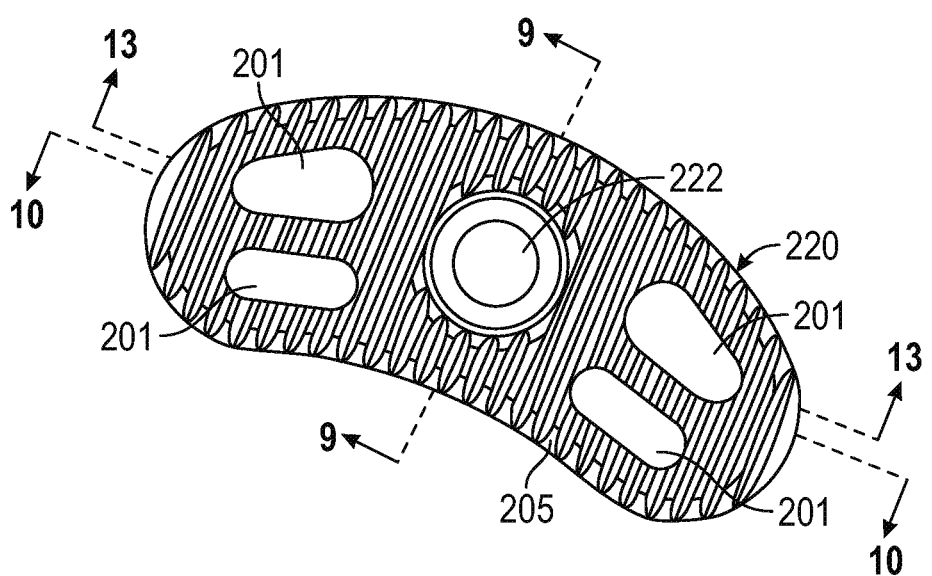
FIG. 11B shows a superior view of the vertical, expandable interbody fusion device of FIG. 7 with the moveable member extended, in accordance with an aspect of the present invention.

Shown in FIG. 7, is an example of the unidirectional vertical expandable interbody fusion device 200. The device 200 as shown in FIGS. 7, 8 and 11A-B has a generally curved or banana shaped geometry. For example purposes, as seen in FIG. 11A-B, the long sides are arcuate although it is contemplated that other geometrical shapes may also be used in the construct, with the end portions being shown as comprised of smaller radiused portions to facilitate insertion and bone coverage. The implant 200 may likely include at least one superior (although the moveable member could be repositioned on the inferior aspect as well) moveable member 220 and a base member 210. The superior or top member 220 may be detachably coupled to the base member 210.

As seen in FIGS. 8, 11A-B, and 13, implant 200 typically has at least two oval shaped through holes 201 for insertion of bone graft material disposed on the inferior and superior bone contacting surfaces 205. For example purposes, FIG. 11A-B shows implant 200 having four holes 201, although, more or less number of holes may be used depending on the clinical situation. These openings typically extend through both bone contacting surfaces 205 and into the inner cavity of the base member 210. The size and configuration of the openings 201 allow the surgeon to place bone graft material inside the inner cavity of the implant 200 to achieve a continuous fusion between the inferior and superior vertebral bodies.

Figure 9:
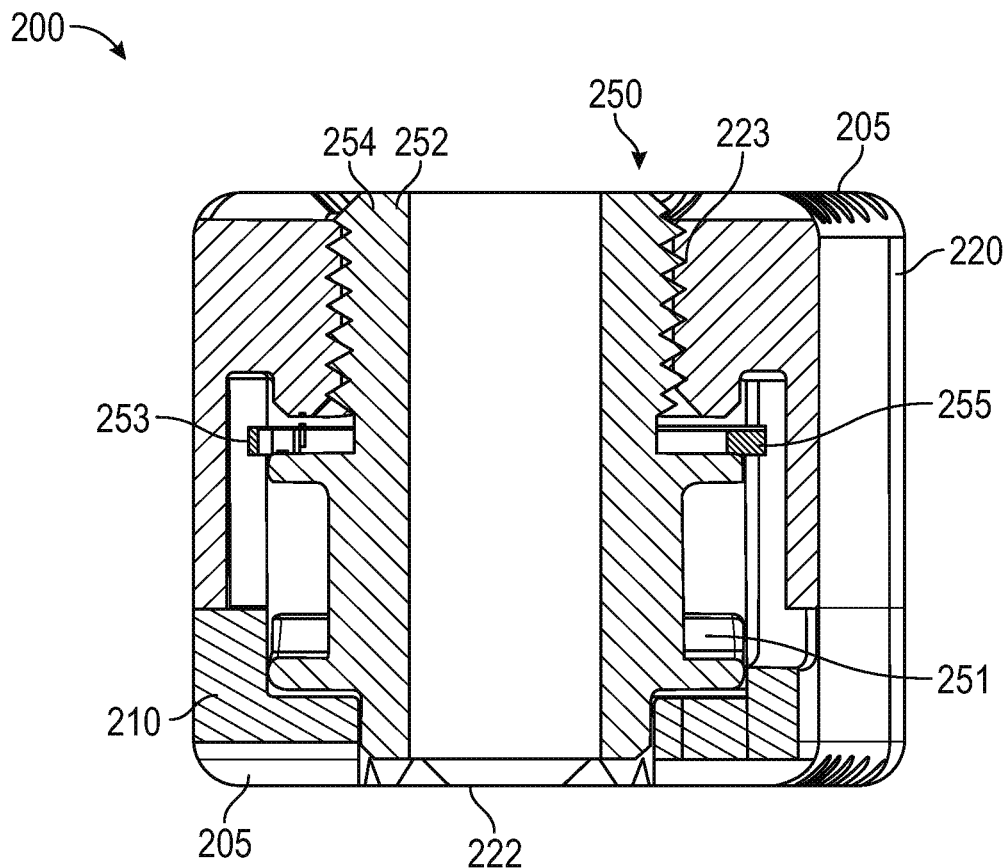
FIG. 9 is an enlarged, width-wise cross-sectional, elevational view of one embodiment of the expandable interbody fusion device of FIG. 7 showing the expansion/retraction mechanism taken along line 9-9 in FIG. 11B, in accordance with an aspect of the present invention.
Figure 10:
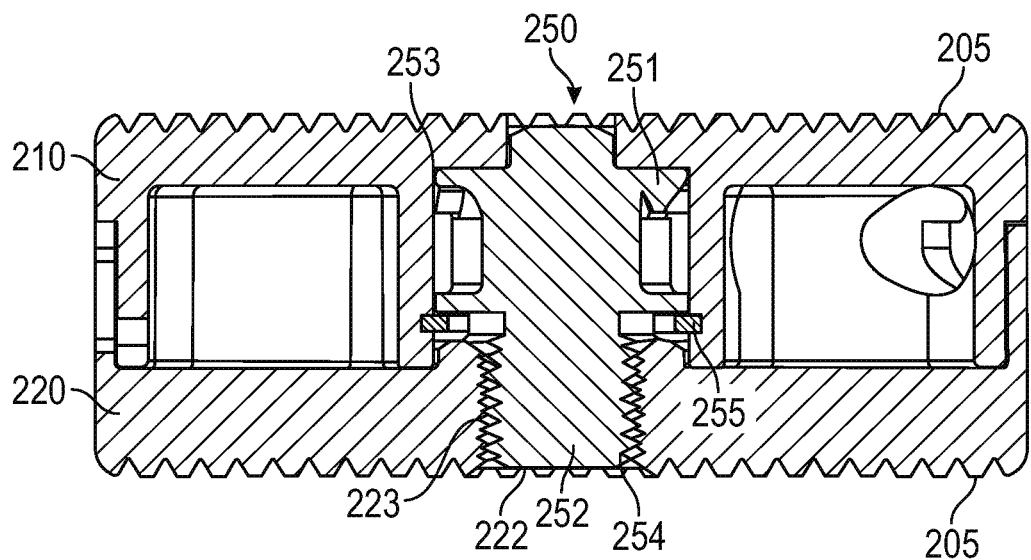
FIG. 10 is an enlarged, lateral cross-sectional, elevational view of the expansion/retraction mechanism of the expandable interbody fusion device of FIG. 7 taken along line 10-10 in FIG. 11B, in accordance with an aspect of the present invention.
Figure 13:
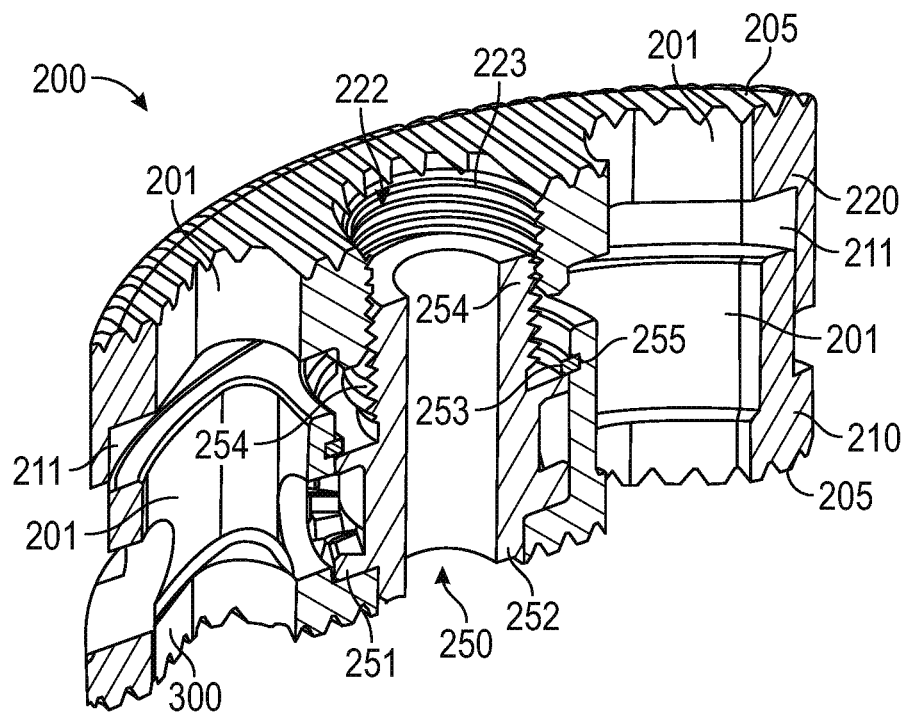
FIG. 13 is a sectional view of the expandable interbody fusion device of FIG. 7 taken along line 13-13 in FIG. 11B, along the plane of the tool insertion hole, in accordance with an aspect of the present invention.

As seen in FIGS. 9, 10, and 13, top member 220 also may have at least one opening 211 oriented in a vertical direction. Openings 211 are configured to facilitate the orientation of the top member 220 as it translates from a retracted to an expanded position and while also keeping it rotationally stationary. The openings 211 may also include a mechanism which may be in the form of a stop pin, flange, lip or other mechanism that keeps the top member 220 from overextending and disengaging from the base member 210.

Figure 8:
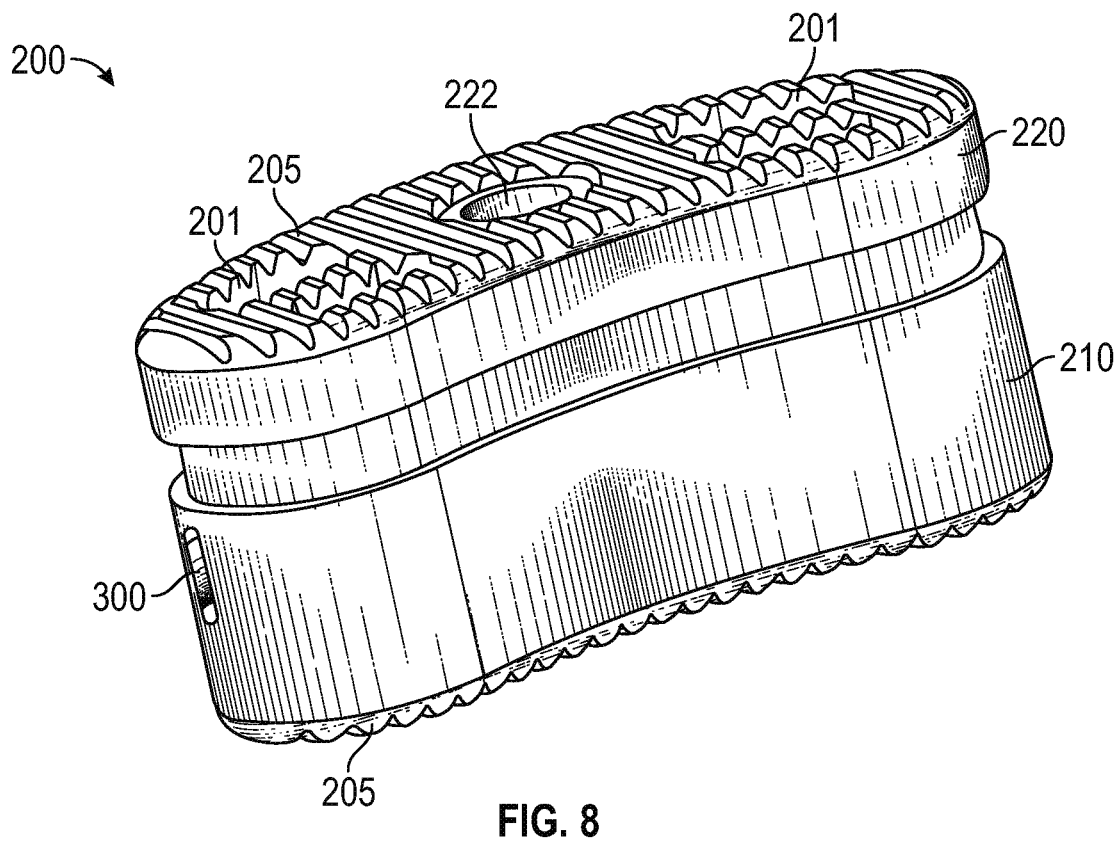
FIG. 8 is a perspective view of the expandable interbody fusion device of FIG. 7 with the vertical moveable member extended, in accordance with an aspect of the present invention.

Again as shown in FIGS. 7, 8, and 13, positioned intermediate the holes 201 is a central through circular hole 222. Housed within hole 222 is a means for extension and retraction of the top member 250. As shown in sectional views depicted in FIGS. 9, 10, and 13, hole 222 may include a non-threaded portion and a threaded portion 223. Positioning of the threaded portion 223 and the non-threaded portions may change depending on the orientation of the implant 200, but generally threaded portion 223 will be located within top member 220. Rotation of the means for extension and retraction 250 will cause top member 220 to move either in a superior or inferior direction relative to the base member 210. The overall height of the implant 200 can be changed via the rotation of the means for extension and refraction 250 and the corresponding unidirectional movement of top member 220. It is contemplated that other means for extension and retraction of top member 220 may include a ratcheting or locking sliding mechanism.

Also shown in FIGS. 7, 8, and 11A-B are the superior and inferior bone contacting surfaces 205. For example purposes, bone contacting surfaces 205 are shown having teeth-like or similar configured structures projecting away from the superior and inferior surfaces. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. Further, it is contemplated that angled bone contacting surfaces, caps or plates may be attachable to address various deformities that are encountered clinically. It is also understood that the bone contacting surfaces 205 may be coated with bioactive or bone ingrowth coatings.

FIGS. 9, 10, and 13 show the means for extension and contraction of the top member 250 (or also known as the extension/contraction means or extension-retraction means) used in the device 200. The extension/contraction means 250 includes a gear 251, a partially threaded rod member 252 and a retaining ring structure 253. The sectional views of FIGS. 9, 10, and 13 show the extension/contraction means 250 positioned within a central or open cavity of base member 210 and oriented in an vertical direction. As depicted, the plane of the gear 251 lies perpendicular to the longitudinal axis of the threaded rod member 252. Therefore, when the gear 251 is rotated, the threaded rod member 252 will turn and cause the engaged top member 210 to translate either in a superior or inferior direction relative to the base member. Typically, the gear 251 is fixed proximate to one of the ends of the threaded rod member 252 with the ring structure 253 generally positioned a distance from the gear 251, although still in the central region of the threaded rod member 252. The extension/contraction means 250 functions to convert rotational movement of the gear 251 to translational movement of the top member 220. The threaded rod member 252 will typically have one threaded portion 254 that engages threaded portion 223 of hole 222 passing through top member 220.

As seen in FIGS. 9, 10, and 13, ring 253 acts to couple the extension/contraction means 250 and maintain the superior and inferior position of the mechanism when rotated. Ring 253 may be a snap ring or other similar type of structure that will nest within a notch 255 or other retainment mode within the inner cavity of the base member 210.

Figure 12:
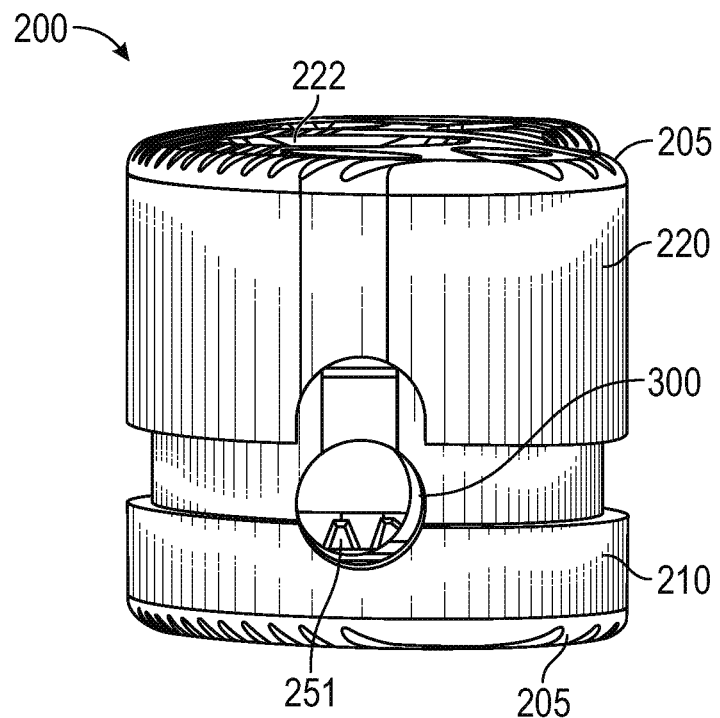
FIG. 12 is a side, elevational view of the expandable interbody fusion device of FIG. 7, showing the tool insertion hole, in accordance with an aspect of the present invention.

Although not shown, the teeth or cogs of gear 251 are sized to mate with a corresponding toothed end of an extension tool. The end of such a tool would usually be inserted into hole 300 (see FIGS. 8, 12, and 13) and then engage gear 251 when the gear teeth mesh with the tool end. Rotation of the tool by the user will cause gear 251 to rotate causing top member 220 to translate as it moves along the threaded portion 223 of the threaded rod member 252.

Referring now to FIGS. 14-19, with particular reference to FIGS. 14-17, a second example of a unidirectional, horizontal expandable interbody fusion device 400 is shown. The device 400 as seen in FIGS. 14-17 has a generally rectangular geometry with various configured long sides to facilitate insertion and bone coverage. For example purposes, the long sides are arcuate although it is contemplated that other geometrical shapes may also be used in the construct. The implant 400 may likely include at least one moveable side member 420 and a body member 410. The side member 420 may be detachably coupled to the body member 410.

Figure 15:
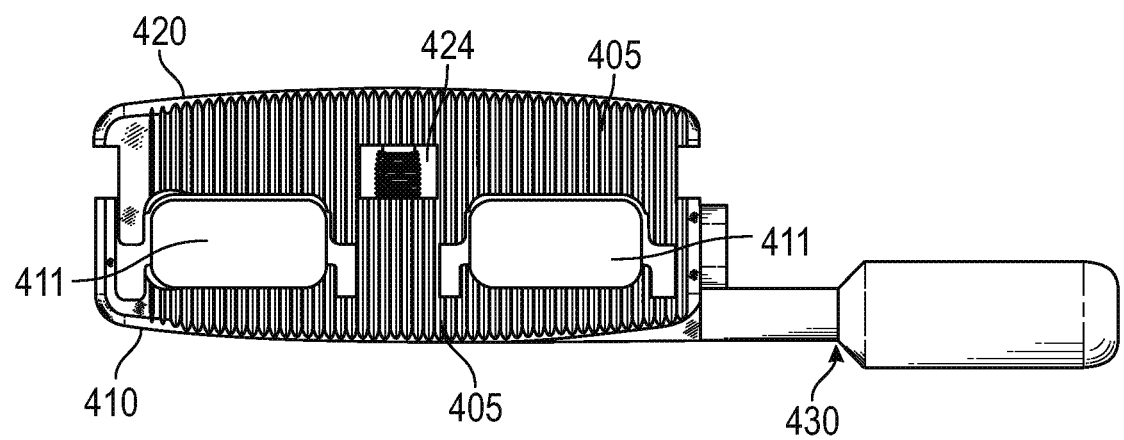
FIG. 15 is a superior view of the expandable interbody fusion device of FIG. 14 with the moveable member extended and the tool inserted into a tool insertion hole, in accordance with an aspect of the present invention.
Figure 18:
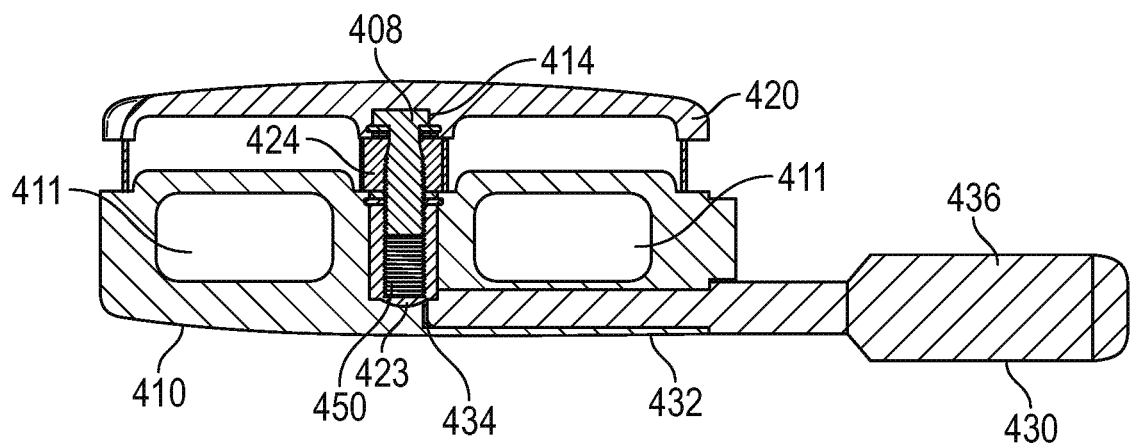
FIG. 18 is a cross-sectional transverse plane, elevational view of one embodiment of the expandable interbody fusion device of FIG. 14 taken along line 18-18 in FIG. 17, in accordance with an aspect of the present invention.

As seen in FIGS. 14, 15, and 18, body member 410 typically has at least two oval shaped through holes 411 for insertion of bone graft material disposed on the inferior and superior bone contacting surfaces 405. The holes extend through these top and bottom surfaces 405 of the body member 410. These openings 411 typically extend through both bone contacting surfaces 405 and into the inner cavity of the body member 410. The size and configuration of the openings 411 allow the surgeon to place bone graft material inside the implant 400 to achieve a continuous fusion between the inferior and superior vertebral bodies.

Figure 16:
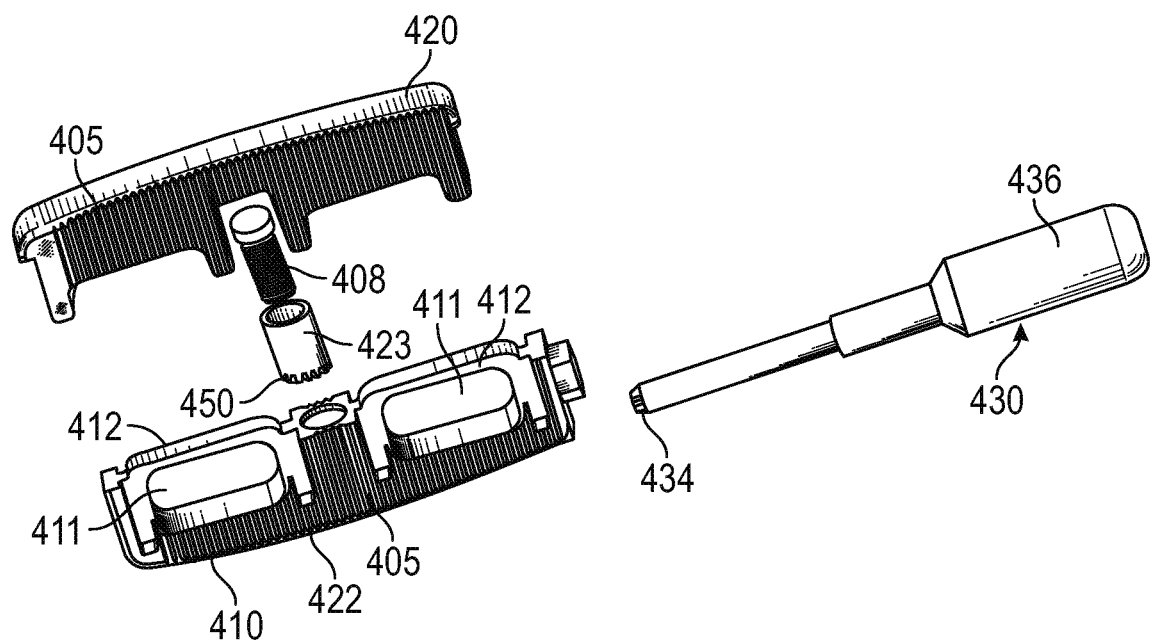
FIG. 16 is an exploded view of the expandable interbody fusion device of FIG. 14, in accordance with an aspect of the present invention.

As seen in FIGS. 15, 18, and 20, side member 420 also may have at least one channel 406 oriented in the horizontal direction. These channels 406 are configured to facilitate the orientation of the side member 420 as it translates from a retracted to an expanded position and vice-a-versa. The implant 400 may also include a mechanism which may be in the form of a screw, stop pin, flange, lip or other mechanism that keeps the side member 420 from overextending and disengaging from the base member 410. As illustrated in FIG. 16, the mechanism is a screw 408.

As shown in FIGS. 16, 18, and 19, the screw 408 may also be used as part of the mechanism for extension and retraction of the side member 420 and may be threaded. A hole 422 may be positioned intermediate the holes 411 in the body member 410. Housed within the hole 422 and the cavity 424 is a means for extension and retraction of the side member 420. The hole 422 is configured to mate with a threaded cylindrical member 423. The threaded cylinder member 423 includes a threaded portion that is configured to threadingly engage with the screw 408. Rotation of the threaded cylindrical member 423 will cause screw 408 to move either in an inward or outward direction relative to the body member 410 thereby moving side member 420 in an inward or outward direction with screw 408. It is also contemplated that the threaded cylindrical member 423 may include both a threaded portion and non-threaded portion. In addition, side member 420 may include a cavity 424 positioned intermediate the holes 411 which is exposed when the side member 420 is extended. The overall width of the implant 400 can be changed via the rotation of the threaded cylindrical member 423 and the corresponding unidirectional movement of the screw 408 which moves the side member 420. It is contemplated that other means for causing the controlled translation of side member 420 to occur may include a ratcheting or locking sliding mechanism.

Also shown in FIGS. 14-16 and 20 are the superior and inferior bone contacting surfaces 405. For example purposes, bone contacting surfaces 405 are shown having teeth-like or tine structures projecting away from the superior and inferior surfaces. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. Further, it is contemplated that angled bone contacting surfaces, caps or plates may be attachable to address various clinical deformities that are encountered clinically. It is also understood that the bone contacting surfaces 405 may be coated with bioactive or bone ingrowth coatings.

As shown in FIG. 16, body member 410 has a generally rectangular shape with two protrusions 412 extending along the transverse plane. The protrusions 412 are configured to engage the above discussed channels 406 of the side member 420 as the side member 420 is moved relative to body member 410. The protrusions 412 are generally positioned in the lateral aspect of body member 410. A centralized hole 422 that for this embodiment is positioned between the above described protrusions 412 is sized to receive the threaded cylindrical member 423 or other means for moving the side member 420.

As shown in the sectional views of FIGS. 18 and 19, the threaded cylindrical member 423 includes a gear 450 to enable the threaded cylindrical member 423 to rotate within the body member 410 and engage the screw 408 causing movement of the side member 420. The sectional views of FIGS. 18 and 19 also show the screw 408 positioned within the central cavity of threaded cylindrical member 423 which is in turn positioned within the central cavity of hole 422 of body member 410. The screw 408 is removably secured in opening 414 in the cavity 424 of the side member 420 to maintain the static position of the expansion/retraction mechanism when rotated.

As shown in FIGS. 16, 18, and 19, a tool 430 may be used to expand and retract the side member 420 from the body member 410. The tool 430 extends through an opening 432 in the body member 410 which extends from the exterior of the body member 410 to the hole 422. The tool 430 includes a toothed end 434 for mating with the gear 450. The gear 450 has teeth or cogs which are sized to mate with the corresponding toothed end 434 of the tool 430. The toothed end 434 of the tool 430 may be inserted into opening 432 of the body member 410 and then engage gear 450 when the gear teeth mesh with the toothed end 434. Rotation of the tool 430 at the handle 436 by a user will rotate the toothed end 434 of the tool 430 causing the gear 450 to rotate thereby rotating the threaded cylindrical member 423. Rotation of the threaded cylindrical member 423 causes screw 408 to translate in the threaded cylindrical member 423 thereby moving the side member 420 along. The threaded cylinder member 423 and screw 408 function to convert rotational movement of the gear 450 by the tool 430 to translational movement of the side member 420.

The biocompatible materials used to fabricate the dynamic horizontal implant 100, the dynamic vertical implant 200, and the second dynamic horizontal implant 400 could include a myriad of metals, polymers and composites. Examples of these include PEEK, titanium and stainless steel.

The example surgical method for using any of the interbody fusion devices 100, 200, 400 is well known in the art, including the appropriate surgical exposure and dissection techniques. The method includes, obtaining the properly sized and configured device 100, 200, 400 relative to the target vertebral end plates that will be opposing the superior and inferior surfaces 105, 205, 405. An expansion or extension tool, such as 430, is then inserted into the hole 122, 300 or opening 432 of the device 100, 200, 400 to secure it for insertion into the spine. For example purposes only, we shall describe herein the technique as used in the insertion between two vertebral bodies to maintain the disc space there between. The device 100, 200, 400 is usually slid from a lateral or posterior-lateral direction into the target disc space.

Following positioning of the device 100, 200, 400 within the disc space, the extension/expansion/insertion tool is rotated causing either the side member 120, 420 or top member 220 to move away from the body or base member 110, 210, 410 resulting in the overall width dimension or height dimension of the device 100, 200, 400 to increase or decrease, depending upon the direction of the rotation of the extension/contraction means. The user will stop rotating the extension/expansion tool once optimum support is achieved relative to the inferior and superior vertebral bodies for implant 100, the stop pins 112 are engaged by the side member 120 thus, restraining any further translation of the side member 120.

The method may further include the step of detaching the extension/expansion tool from the body or base member 110, 210, 410 and removing the instrument from inside the living body.

It should be understood by those skilled in the art that the surgical method described herein may also include alternatively, using modular bone contacting plates or surfaces which have been coupled in some manner to an alternative embodiment of the body or base member 110, 210, 410 or side member 120, 420 or top member 210 to accommodate various clinical deformities or bone growth coatings.

Although the example embodiments have been depicted and described in detail herein, it will be apparent to those skilled in the relevant art that various modifications, additions and substitutions can be made without departing from its essence and therefore these are to be considered to be within the scope of the following claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of using an interbody fusion device, comprising:
    preparing a space between two adjacent vertebral bodies;
    obtaining an interbody fusion device, wherein the interbody fusion device comprises:
        a top member having a first bone-engaging surface and a threaded opening;
        a base member received by the top member, the base member having a second bone-engaging surface and an open cavity aligned with the threaded opening of the top member;
        an expansion member disposed within the open cavity for rotation about an axis, the expansion member having a threaded portion configured to threadably engage with the threaded opening and a central bore to maintain an opening through the threaded opening in the first bone-engaging surface through the open cavity in the second bone-engaging surface; and
        a support ring coupled to the base member within the open cavity, the support ring configured to retain the expansion member within the base member in a fixed position along the axis relative to the second bone-engaging surface;
        wherein the expansion member further comprises a gear portion and a radially extending portion disposed between the gear portion and the threaded portion, the radially extending portion disposed adjacent the support ring; and
    using an expansion tool to move the top member in a direction relative to the base member, wherein the support ring is positioned in a notch inset into the base member to secure the top member within the base member.

2. The method of claim 1, wherein the gear portion includes a first side and a second side with the first side having a plurality of gear teeth and the second side being in contact with the base member.

3. The method of claim 1, wherein the gear portion includes a plurality of axially extending gear teeth.

4. The method of claim 3, wherein the base member includes a tool insertion opening in communication with the open cavity.

5. The method of claim 4, wherein the method further comprises:
obtaining the expansion tool, the expansion tool comprising a handle, a shaft having a first end and a second end, wherein the first end is connected to the handle and the second end is configured for engagement with the expansion member.

6. The method of claim 5, wherein the method further comprises:
inserting the expansion tool into the tool insertion opening and engaging the second end of the expansion tool with the expansion member.

7. The method of claim 6, wherein using the expansion tool to move the top member in a direction relative to the base member comprises:
rotating the expansion tool to move at least one of the first bone-engaging surface or second bone-engaging surface.

8. The method of claim 7, wherein the first bone-engaging surface includes at least one first through hole, and the second bone-engaging surface includes at least one second through hole aligned with the at least one first through hole.

9. The method of claim 7, wherein using the expansion tool to move the top member in a direction relative to the base member comprises:
rotating the expansion member about a first axis extending transverse to the first bone-engaging surface and the second bone-engaging surface;
threadably engaging the expansion member with the threaded opening of the top member; and
translating the first bone-engaging surface away from the second bone-engaging surface along the first axis to contact the two adjacent vertebral bodies.

10. The method of claim 9, wherein the expansion tool is rotated about a second axis that is transverse to the first axis to rotate the expansion member.

11. The method of claim 1, wherein the method further comprises:
inserting the interbody fusion device into the space.

12. The method of claim 1, wherein the support ring is non-threaded.

13. A surgical method for maintaining a space between two vertebral bodies in a spine, the method comprising:
obtaining a movable interbody implant, the implant comprising:
a top member having a superior bone-engaging side and a threaded opening;
a base member configured to be received by the top member, the base member having an expansion tool opening, an inferior bone-engaging side and an open cavity in communication with the threaded opening of the top member and expansion tool opening;
an expansion member positioned within the open cavity for rotation about an axis extending transverse to the superior and inferior bone-engaging sides, the expansion member having a threaded portion threadably engaged with the threaded opening and a central bore to maintain an opening through the threaded opening in the superior bone-engaging side through the open cavity in the inferior bone-engaging side, and
a support ring coupled to a notch inset into the base member within the open cavity, the support ring configured to retain the expansion member within the base member in a fixed position along the axis relative to the inferior bone-engaging side,
wherein rotation of the expansion member moves the top member relative to the base member along the axis, while the support ring maintains the fixed position of the expansion member relative to the inferior bone-engaging side along the axis;
inserting the movable interbody implant into a space between two vertebral bodies.

14. The surgical method of claim 13, wherein the method further comprises:
expanding the movable interbody implant by rotating the expansion member about the axis until the superior bone-engaging side and inferior bone-engaging side pressingly contact the two vertebral bodies.

15. A surgical method for maintaining a space between two bones, the method comprising:
obtaining a movable surgical implant, the implant comprising:
a top member having a first bone-engaging side and a threaded opening;
a base member received by the top member, the base member having a second bone-engaging side and an open cavity in communication with the threaded opening of the top member;
an expansion member secured within the open cavity for rotation about an axis extending transverse to the first and second bone-engaging sides, the expansion member having a threaded portion threadably engaged with the threaded opening and a central bore to maintain an opening through the threaded opening in the first bone-engaging side through the open cavity in the second bone-engaging side, and
a support ring fixed to the base member within the open cavity, the support ring configured to secure the expansion member within the base member in a fixed position along the axis relative to the second bone-engaging side,
wherein rotation of the expansion member translates the top member relative to the base member along the axis;
wherein the support ring is configured to be snapped into a notch in the base member within the open cavity to retain the expansion member within the base member; and
wherein the expansion member further comprises a first end opposite the threaded portion, and a radially extending portion disposed between the first end and the threaded portion, the radially extending portion disposed adjacent the support ring; and
using an expansion tool to move the top member in a direction relative to the base member.

16. The surgical method of claim 15, wherein using an expansion tool to move the top member in a direction relative to the base member comprises:
inserting the movable surgical implant into a space between two bones; and
enlarging the movable surgical implant by rotating the expansion member about the axis until the first bone-engaging side and second bone-engaging side pressingly contact the two bones.

17. The method of claim 15, wherein the support ring is non-threaded.

* * * * *